United States Patent [19]

Bell

[11] 4,129,603

[45] Dec. 12, 1978

[54] MANUFACTURE OF HALOGENATED COMPOUNDS

[75] Inventor: Stephen L. Bell, Runcorn, England

[73] Assignee: Imperial Chemical Industries Limited, London, England

[21] Appl. No.: 875,935

[22] Filed: Feb. 7, 1978

[51] Int. Cl.² ............................................. C07C 17/20
[52] U.S. Cl. ................................. 260/653; 260/653.7
[58] Field of Search .............................. 260/653, 653.7

[56] References Cited

U.S. PATENT DOCUMENTS 3,755,477  8/1973  Firth et al. .................... 260/653.7

*Primary Examiner*—C. Davis
*Attorney, Agent, or Firm*—Cushman, Darby & Cushman

[57] ABSTRACT

Manufacture of 1,1,1,2-tetrafluorethane by reacting 1,1,1-trifluoro-2-chloroethane with hydrogen fluoride in the presence of a chromium oxide catalyst and reducing the 1,1-difluoro-2-chloroethylene content of the impure 1,1,1,2-tetrafluoroethane product by intimately contacting the impure product with an aqueous solution of a metal permanganate.

14 Claims, No Drawings

MANUFACTURE OF HALOGENATED COMPOUNDS

This invention relates to a process for the manufacture of 1,1,1,2-tetrafluoroethane and in particular to such a process wherein said tetrafluoroethane of a high degree of purity is obtained.

A process is disclosed in Ser. No. 875,934, filed Feb. 7, 1978, for the manufacture of 1,1,1,2-tetrafluoroethane which comprises reacting in the vapour phase at elevated temperature, suitably in the range 300° C. to 400° C., a haloethane of formula $CX_3CH_2Y$ wherein X is bromine, chlorine or fluorine and Y is either bromine or chlorine with hydrogen fluoride in the presence of a catalyst which is chromium oxide or which is at least in part basic chromium fluoride.

In said process the chromium oxide catalyst may consist of chromium oxide alone. The chromium oxide may be activated by heating in an inert atmosphere. Again the catalyst may comprise a basic chromium fluoride in which chromium is associated with oxygen and fluorine atoms. When employing a chromium oxide catalyst prepared by heating a readily-decomposable salt of chromium e.g. chromic hydroxide in air or oxygen as described in our U.S. Pat. No. 3,426,009 useful yields of the desired 1,1,1,2-tetrafluoroethane may be obtained.

It is particularly preferred in said process to employ a chromium oxide catalyst which is obtained by treating a chromium hydroxide paste in an atmosphere comprising 10 to 100 percent by weight of steam at temperatures of 50° C. to 180° C. for a least 1 hour and subsequently drying and calcining the product as is more fully described and claimed in our U.S. Pat. No. 3,755,477. The catalyst may be compressed into pellets and used in a fixed bed. Alternatively the catalyst of appropriate particle size may be used in a fluidised bed. The pelleted or non pelleted catalyst may be given a prefluorination treatment by passing hydrogen fluoride over the catalyst at 250° C. to 450° C. for at least 30 minutes. In any event the catalyst may take up variable amounts of fluorine in use.

The amount of hydrogen fluoride employed in said process depends to a great extent on the haloethane starting material. At least the stoichiometric amount of hydrogen fluoride is usually employed per mole of haloethane starting material. It is preferred to employ an excess of the stoichiometric amount but not greater than six times the stoichiometric amount of hydrogen fluoride in the present process. It is particularly preferred to employ at least two moles but not greater than six moles of hydrogen fluoride per mole of said organic starting material, e.g. 1,1,1,-trifluoro2-chloroethane.

Suitable temperatures in said process are in the range 300° C. to 400° C. for example 325° C. to 375° C. Preferred contact times are in the range 2 to 60 seconds. Atmospheric or superatmospheric pressures may be employed.

Unreacted organic starting material, hydrogen fluoride and by-products e.g. haloethanes containing chlorine atoms in the $CX_3$ group may be recycled to the process for further reaction to give the desired compound.

However when the Y substituent in the haloethane starting material is chlorine there may be formed in addition to the desired product asym tetrafluoroethane ($CF_3 CH_2F$) a small amount of 1,1-difluoro-2-chloroethylene ($CF_2=CHCl$) as by-product. This occurs for instance when the organic starting material in the hydrofluorination reaction is 1,1,1-trifluoro-2-chloroethane.

It is desirable to reduce further even small amounts of said difluorochloroethylene but this is extremely difficult to achieve by conventional methods, for example by fractional distillation.

We have now found that said difluorochloroethylene impurity contained in 1,1,1,2-tetrafluoroethane may be reduced in content by intimately contacting said impure asym tetrafluoroethane with a metal permanaganate in a liquid medium.

The purification process of the present invention is applicable to the purification of asym tetrafluoroethane containing difluorochloroethylene impurity, whatever the source of the impure asym tetrafluoroethane. The purification process is however especially applicable to the asym tetrafluoroethane product obtained by the process described in said copending Application.

According to a feature of the present invention we provide a process for the manufacture of 1,1,1,2-tetrafluoroethane which comprises reacting in the vapour phase at elevated temperatures a haloethane of formula $CX_3CH_2Y$ wherein X is bromine, chlorine or fluorine and Y is chlorine with hydrogen fluoride in the presence of a catalyst which is chromium oxide or which is at least in part basic chromium fluoride and wherein the 1,1,1,2-tetrafluoroethane product containing 1,1-difluoro-2-chloroethylene as impurity is intimately contacted with a metal permanganate in a liquid medium whereby said haloethylene content is reduced.

Preferably as in said copending Application the X substituent in the organic starting material is chlorine and/or fluorine. Preferably also at least one of the X substituents is fluorine. A very suitable haloethane starting material is 1,1,1-trifluoro-2-chloroethane.

The impure asym tetrafluoroethane (1,1,1,2-tetrafluoroethane) to be treated to remove the haloethylene impurity may be the crude product which is associated with other haloethanes containing fluorine including one or more of 1,1,1,2,2-pentafluoroethane ($CF_3 CHF_2$), 1,1,1,2-tetrafluoro-2-chloroethane ($CF_3 CHClF$), 1,1,1-trifluoroethane ($CF_3 CH_3$) and 1,1,1-trifluoro-2-chloroethane ($CF_3 CH_2Cl$).

Such a crude reaction product may be obtained by bringing 1,1,1-trifluoro-2-chloroethane into reaction with hydrogen fluoride at temperatures in the range 300° C. to 400° C. in the presence of a catalyst which is chromium oxide or which is at least in part basic chromium fluoride as is previously described.

However the crude product may be fractionally distilled to give an impure product consisting essentially of 1,1,1,2-tetrafluoroethane and 1,1-difluoro-2-chloroethylene as impurity.

Preferably there are used aqueous, or non-aqueous solvents for the permanganate particularly organic solvents or mixture thereof, which are not appreciably attached by permanganate. It is particularly suitable to use the permanganate in the form of an aqueous solution.

The permanganate may be in particular an alkali metal or alkaline earth metal permanganate and the permanganate solution may be acid, neutral or alkaline. Of the latter a neutral or alkaline solution is preferred. If the solution is to be alkaline this may be achieved most conveniently by addition of an alkali metal hydroxide although other bases may be used if desired, for example alkaline earth metal hydroxides or ammonia.

Useful results can be obtained when using from 0.1% to 10% by weight in the aqueous phase of sodium hydroxide or potassium hydroxide. Lower rather than higher proportions than 10% by weight of NaOH or KOH are preferred and it is particularly preferred to employ concentrations from 0.5% up to 2% by weight NaOH or KOH in the aqueous phase.

Sodium and potassium permanganates are particularly useful metal permanganates. Useful results may be obtained with various concentrations of permanganate in the aqueous phase. For example good results are obtained when using 20 g/l to 60 g/l potassium permanganate in the aqueous phase.

The temperature used in the treatment with aqueous permanganate is usually in the range 10° C. up to the boiling point of the mixture, for example 15° C. to 40° C.

The time of treatment with aqueous permanganate may vary according to the process conditions. For example treatment times in the range 5 minutes to 90 minutes can be employed.

The relative proportions of aqueous solution of permanganate to crude asym tetrafluoroethane may be varied considerably and the optimum proportions will depend on such factors as thoroughness of mixing, the amount of the impurity, the temperature of treatment and composition of the product. Thus the proportion by volume of aqueous permanganate to crude organic material is usually in the range 1:0.1 to 1:10, for example 1:0.2 to 1:6.

After agitation of the organic material with aqueous permanganate the mixture is allowed to separate into two distinct layers and the purified lower asym tetrafluorethane can be fractionally distilled.

1,1,1,2-tetrafluoroethane which has a low boiling point (−26.5° C.) is useful as a refrigerant, for example, in food-freezing techniques. It is useful as an aerosol propellant and as a foam blowing agent.

The following Example illustrates the invention. All percentages are v/v unless otherwise stated.

EXAMPLE

Into a tubular nickel reactor 90 cms long and 2.5 cms internal diameter were placed 150 grams of a chromium oxide catalyst. The latter had been prepared by steam treatment of a chromium hydroxide paste at 95° C. for 18 hours, and subsequently calcined at 340° C. for 11 hours as described in our U.S. Pat. No. 3,755,477. The catalyst was then pretreated with hydrogen fluoride at 350° C. for 4 hours.

The tubular reactor was heated by an electric furnace and the temperature inside the reactor was held at 350° C.

1827 grams of 1,1,1-trifluoro-2-chloroethane were passed together with an amount of hydrogen fluoride over the catalyst over a total period of 55 hours. The molar ratio of HF:CF$_3$CH$_2$Cl was 4:1. The contact time was 7 seconds.

The products were collected, washed with water, scrubbed with 2.5% w/w aqueous KOH solutions and dried.

The organic product thus obtained contained 18.2% 1,1,1,2-tetrafluoroethane, 80% 1,1,1-trifluoro-2-chloroethane, 1.65% of a mixture of pentafluoroethane with 1,1,1-trifluoroethane, 0.12% 1,1-difluoro-2-chloroethylene.

A very similar crude organic product containing 16% 1,1,1,2-tetrafluoroethane, 83% 1,1,1-trifluoro-2-chloroethane, 0.8% pentafluoroethane and 1000 ppm 1,1-difluoro-2-chloroethylene contaminant was obtained using the same method of manufacture as above except that the molar ratio of HF: CF$_3$CH$_2$Cl was 3.3:1.

Samples were taken of an aqueous solution of permanganate containing 10g NaOH, 60g KMnO$_4$ and 1500g water. These were placed together with the latter, crude organic product in an autoclave in various ratios and were vigorously stirred at different temperatures under autogeneous pressure. After the runs the mixtures were allowed to settle and the lower organic layer was recovered and analysed for remaining 1,1-difluoro-2-chloroethylene content. The results are indicated in the Table.

TABLE

| KMnO$_4$/Organics ratio | Temp °C | Time mins | Remaining CF$_2$=CHCl ppm in organic product |
|---|---|---|---|
| 1.1 | 30° C | 15 | 5 |
|  | 30° C | 90 | Not detectable |
| 1:5 | 20° C | 60 | 5 |
| 1:0.2 | 20° C | 20 | 10 |
|  |  | 30 | 7 |
|  | 30° C | 20 | 7.5 |
|  |  | 30 | 5 |

What is claimed is:

1. A process for the manufacture of 1,1,1,2-tetrafluoroethane which comprises reacting in the vapour phase at elevated temperature a haloethane of formula CX$_3$CH$_2$Y wherein X is bromine, chlorine or fluorine and Y is chlorine with hydrogen fluoride in the presence of a catalyst which is chromium oxide or which is at least in part basic chromium fluoride and wherein the 1,1,1,2-tetrafluoroethane product containing 1,1-difluoro-2-chloroethylene as impurity is intimately contacted with a metal permanganate in a liquid medium whereby said haloethylene content is reduced.

2. A process as claimed in claim 1 in which in the haloethane starting material X is chlorine and/or fluorine.

3. A process as claimed in claim 2 in which at least one of the X substituents is fluorine.

4. A process as claimed in claim 3 in which the haloethane is 1,1,1-trifluoro-2-chloroethane.

5. A process as claimed in claim 1 in which the impure 1,1,1,2-tetrafluoroethane in intimately brought in contact with an aqueous solution of a permangante.

6. A process as claimed in claim 5 in which the metal permanganate is an alkali metal or alkaline earth metal permangante.

7. A process as claimed in claim 6 in which the solution of the permangante is neutral or alkaline.

8. A process as claimed in claim 6 or claim 7 in which the metal permanganate is potassium permanagante.

9. A process as claimed in claim 8 in which the concentration of potassium permangante in the aqueous phase is 20 g/liter to 60 g/litre.

10. A process as claimed in claim 5 in which the treatment with the aqueous solution is carried out at a temperature in the range 10° C. up to the boiling point of the mixture.

11. A process as claimed in claim 10 in which the treatment with the aqueous solution is carried out at a temperature in the range 15° C. to 40° C.

12. A process as claimed in claim 5 wherein the proportion by volume of aqueous permanganate to the said impure product is in the range 1:0.1 to 1:10.

13. A process for the reduction of 1,1-difluoro-2-chloroethylene impurity contained in 1,1,1,2-tetrafluoroethane which comprises intimately contacting said impure 1,1,1,2-tetrafluoroethane with a metal permanganate in a liquid medium.

14. A process as claimed in claim 13 in which the impure 1,1,1,2-tetrafluoroethane is intimately brought into contact with an aqueous solution of a metal permanganate.